(12) United States Patent
Hirahara (10) Patent No.: US 9,050,597 B2
(45) Date of Patent: Jun. 9, 2015

(54) PCR METHOD AND PCR DEVICE

(75) Inventor: Shuzo Hirahara, Yokohama (JP)

(73) Assignee: Fluid Incorporated, Yokohama (JP)

( * ) Notice: Subject to any disclaimer, the term of this patent is extended or adjusted under 35 U.S.C. 154(b) by 97 days.

(21) Appl. No.: 12/917,833

(22) Filed: Nov. 2, 2010

(65) Prior Publication Data
US 2011/0212492 A1 Sep. 1, 2011

(30) Foreign Application Priority Data
Nov. 4, 2009 (JP) ................................ 2009-252811

(51) Int. Cl.
| C12Q 1/68 | (2006.01) |
|---|---|
| C12P 19/34 | (2006.01) |
| B01L 7/00 | (2006.01) |
| B01L 3/00 | (2006.01) |
| C07H 21/02 | (2006.01) |
| C07H 21/04 | (2006.01) |

(52) U.S. Cl.
CPC ............ B01L 7/52 (2013.01); *B01L 2300/0645* (2013.01); *B01L 2300/0832* (2013.01); B01L 3/5027 (2013.01); *B01L 2300/0816* (2013.01); *B01L 2300/1833* (2013.01); *B01L 2400/0472* (2013.01); *B01L 2400/0487* (2013.01); *C12Q 1/686* (2013.01)

(58) Field of Classification Search
CPC .............. C12Q 1/686; C12Q 2565/607; B01L 2300/0816; B01L 2300/1833; B01L 2400/0472; B01L 2400/0487; B01L 3/5027; B01L 7/52
See application file for complete search history.

(56) References Cited

U.S. PATENT DOCUMENTS

| 5,965,410 | A | 10/1999 | Chow et al. |
|---|---|---|---|
| 6,406,893 | B1 | 6/2002 | Knapp et al. |
| 2002/0072054 | A1 * | 6/2002 | Miles et al. ........................ 435/6 |
| 2005/0064423 | A1 | 3/2005 | Higuchi et al. |
| 2008/0237046 | A1 | 10/2008 | Hirahara et al. |

FOREIGN PATENT DOCUMENTS

| JP | J08-322569 A | 12/1996 |
|---|---|---|
| JP | H09-094086 A | 4/1997 |
| JP | 2009-529909 A | 8/2009 |
| WO | WO-03-057875 A1 | 7/2003 |
| WO | WO-2007-107947 A1 | 9/2007 |

OTHER PUBLICATIONS

Cetin, et al., "Effect of Joule Heating on Electrokinetic Transport," Electrophoresis, vol. 29, No. 5, Mar. 2008, pp. 994-1005.
Hu, et al., "Electrokinetically Controlled Real-Time Polymerase Chain Reaction in Microchannel Using Joule Heating Effect," Analytica Chimica Acta, vol. 557, Nov. 2005, pp. 146-151.
Heap, et al. "PCR Amplification Using Electrolytic Resistance for Heating and Temperature Monitoring," Biotechniques, vol. 29, No. 5, Nov. 2000, pp. 1006-1012.
Duwensee, et al., "Electrochemical Product Detection of an Asymmetric Convective Polymerase Chain Reaction," Biosensors and Bioelectronics, vol. 25, No. 2, Oct. 2009, pp. 400-405.
Gui, et al., "Analytical and Numerical Study of Joule Heating Effects on Electrokinetically Pumped Continuous Flow PCR Chips," Langmuir, vol. 24, No. 6, Mar. 2008, pp. 2938-2946.
European Search Report for European Patent Application No. 10189746.0 issued on May 3, 2011.
Chunsun Zhang et al., "PCR microfluidic devices for DNA amplification," Biotechnology Advances, vol. 24, No. 3, May 1, 2006, pp. 243-284.
Seth Stern et al., "Microfluidic Thermocyclers for Genetic Analysis," 2002 Inter Society Conference on Thermal Phenomena, pp. 1033-1038.
EPO Communication dated Jul. 4, 2012, issued for the European Patent Application No. 10 189 746.0.
EPO Communication dated Feb. 28, 2014 in corresponding EP Appln No. 10 189 746.0.
Office Action dated Oct. 15, 2014 in connection with the corresponding Japanese Patent Application No. 2009-252811.

\* cited by examiner

*Primary Examiner* — Teresa E Strzelecka
(74) *Attorney, Agent, or Firm* — Locke Lord LLP; James E. Armstrong, IV; George N. Chaclas (57) ABSTRACT

Provided on an inner surface of a container to carry out polymerase chain reaction (PCR) are an electrode pair 22 to be disposed to face each other with a gap along a flow of a reaction solution interposed therebetween, and an AC voltage is applied to the electrode pair 22 to make an AC current flow through the reaction solution, whereby Joule heat is generated to control the reaction solution in temperature. Accordingly, a PCR method and a PCR device that allow generating sufficient Joule heat for a PCR cycle even when an applied voltage is low, and do not electrolyze a reaction solution even by making an electric current flow through the reaction solution can be provided.

15 Claims, 6 Drawing Sheets

PCR METHOD AND PCR DEVICE

TECHNICAL FIELD

The present invention relates to a PCR (polymerase chain reaction) method and a PCR device, and particularly, to a PCR method and a PCR device that have a high response rate to temperature control.

BACKGROUND ART

A conventional PCR method uses an external heater as a means for raising the temperature of a reaction solution for a PCR cycle, and heat of the heater is transmitted to the reaction solution via a wall of a reaction container to heat the reaction solution. However, in this case, the wall is first heated, and the reaction solution is heated by heat of the wall, and thus the response rate of temperature control is low, and heat is diffused along the wall to result in poor energy efficiency.

Therefore, it has been proposed to make electric current flow through a reaction solution to directly heat the reaction solution by Joule heat (refer to, for example, Non Patent Literature 1).

CITATION LIST

Non Patent Literature

[Non Patent Literature 1] Guoqing Hu et al., "Electrokinetically controlled real-time polymerase chain reaction in microchannel using Joule heating effect", Analytica Chimica Acta, vol. 557, (2006) pp. 146-151.

SUMMARY OF INVENTION

Technical Problem

However, because the conventional PCR method using Joule heating makes a DC current flow through a reaction solution, the reaction solution is electrolyzed to produce unnecessary gas on the periphery of the electrodes, and produce unnecessary acidic and alkaline solutions, and thus addressing the same is necessary, and because a voltage is applied to both ends of a long channel, a high voltage must be applied to generate necessary Joule heat, causing a large load on the circuit.

In view of the above problems, it is an object of the present invention to provide a PCR method and a PCR device that allow generating sufficient Joule heat for a PCR cycle even when an applied voltage is low, and do not electrolyze a reaction solution even by making an electric current flow through the reaction solution.

Solution to Problem

A PCR method of the present invention is a method of providing, on an inner surface of a container to carry out polymerase chain reaction (PCR), an electrode pair to be disposed to face each other with a gap along a flow of a reaction solution interposed therebetween, and applying an AC voltage to the electrode pair to make an AC current flow through the reaction solution, thereby generating Joule heat to control the reaction solution in temperature.

Moreover, a PCR device of the present invention comprises: a container to carry out polymerase chain reaction (PCR); an electrode pair disposed to face each other with a gap along a flow of a reaction solution interposed therebetween; and a control unit which applies an AC voltage to the electrode pair to make an AC current flow through the reaction solution, thereby generating Joule heat to control the reaction solution in temperature.

Moreover, as a result of the container being a tubular channel, as compared with a slight amount of reaction solution within the channel, large electrodes can be used, and thus the response rate of the reaction solution temperature to voltage application can be increased.

Moreover, as a result of the channel being vertically oriented, an upward flow of the reaction solution by Joule heating can be used.

Moreover, as a result of the container being a flat chamber which is vertically erected, and the electrode pair being disposed to face each other with a vertical gap interposed therebetween on an inner surface of one of the sidewalls of the chamber, the reaction solution can be circulated within the chamber to perform a PCR cycle.

Moreover, as a result of the container being a flat chamber which is vertically erected, and the electrode pair being disposed to face each other, with the chamber interposed as a gap therebetween, on an inner surface of one of the sidewalls of the chamber and an inner surface of the other sidewall, the reaction solution can also be circulated within the chamber to perform a PCR cycle.

Advantageous Effects of Invention

The present invention allows generating sufficient Joule heat for a PCR cycle even when an applied voltage is low, and does not electrolyze a reaction solution even by making an electric current flow through the reaction solution.

DESCRIPTION OF EMBODIMENTS

Hereinafter, modes for carrying out the present invention will be described in detail with reference to the accompanying drawings.

EXAMPLE 1

Figure 1A:
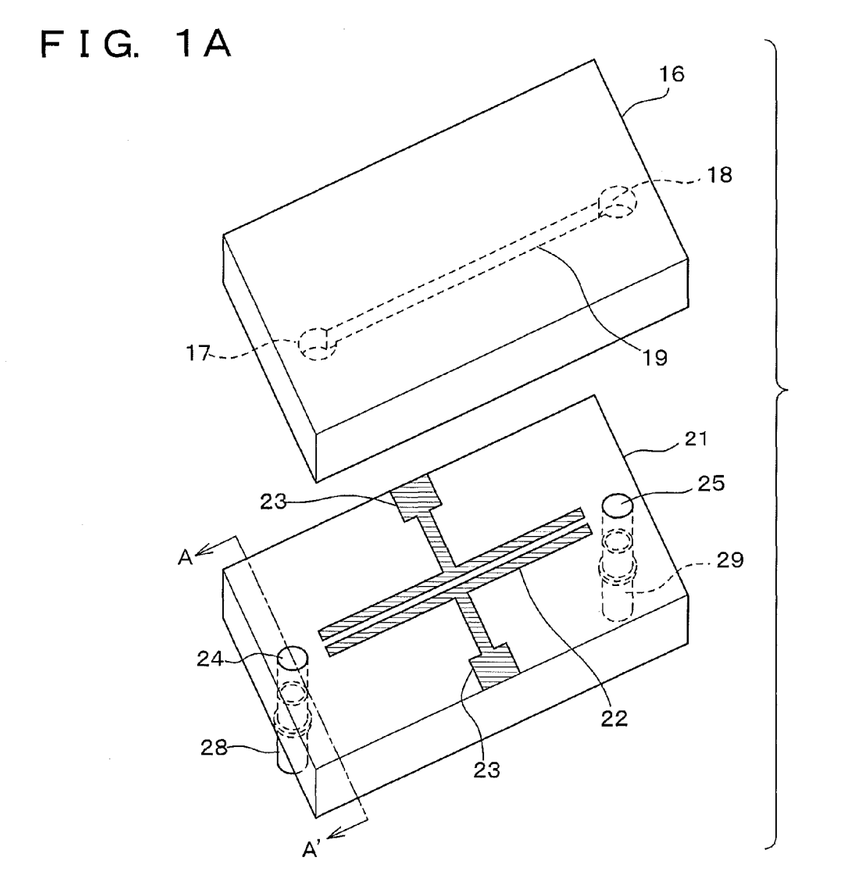
FIG. 1A is an exploded perspective view depicting a configuration of a reaction container of a PCR device according to Example 1 of the present invention.
Figure 1B:
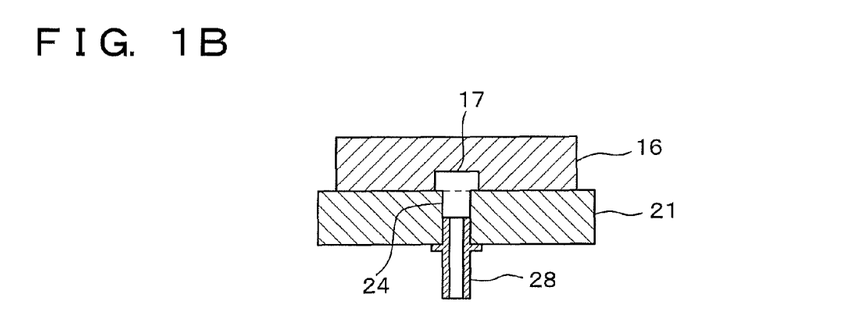
FIG. 1B is a sectional view of FIG. 1A.

FIG. 1A is an exploded perspective view depicting a configuration of a reaction container of a PCR device according to Example 1 of the present invention, and FIG. 1B is a sectional view of FIG. 1A. FIG. 1B is a sectional view along an AA' plane in the case of combination of FIG. 1A. The PCR device of the present example includes a channel forming plate 16 and a substrate 21. The substrate 21 is made of glass, and patterned on an upper surface thereof with an electrode pair 22 prepared by evaporating thin chrome and thereon gold, and the electrode pair 22 has outgoing portions 23 connected by wiring therefrom. The electrode pair 22 has a gap width of 10 μm to 500 μm, for example, 50 μm, and a length of 2 mm to 8 mm, for example, 5.2 mm. The substrate 21 and the channel forming plate 16 form a linear tubular channel 19. The channel forming plate 16 is made of PDMS (polydimethylsiloxane), disposed by being bonded on the substrate 21, provided on a lower surface thereof with a groove to form the channel 19, and provided at one end of the channel 19 with an inlet well 17 of a reaction solution and at the other end with an outlet well 18 of the reaction solution. The channel 19 has, for example, a width of 980 μm, a depth of 600 μm, and the same length as that of the electrode pair 22. At parts of the substrate 21 being in contact with the inlet well 17 and the outlet well 18 provided at both ends of the channel 19, through-holes 24, 25 are opened in the thickness direction, and grommets 28, 29 are fixed on a lower surface side of the through-holes 24, 25. Tubes are connected to these grommets 28, 29 to let the reaction solution flow in and out.

Figure 2:
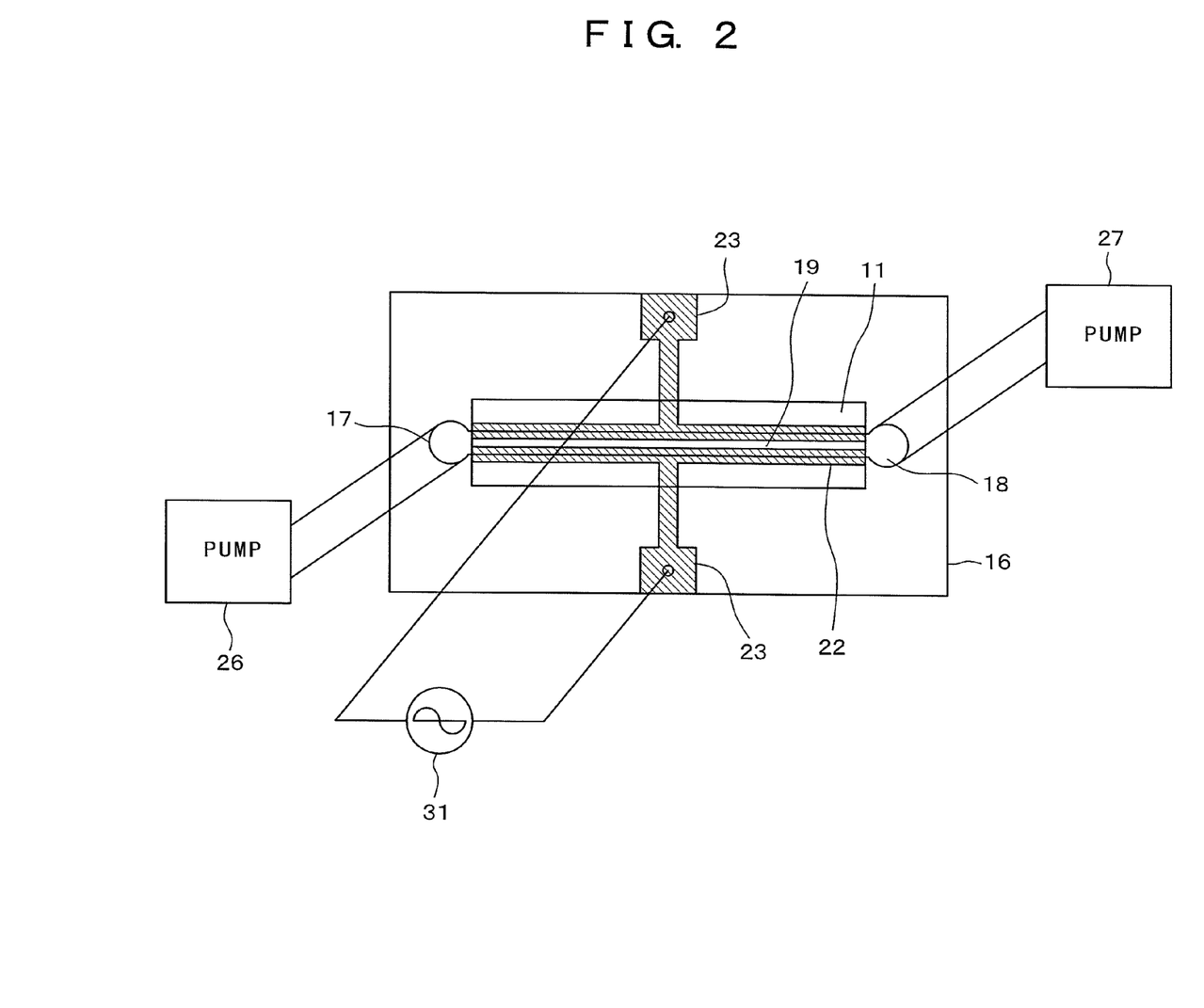
FIG. 2 is a top view of the reaction container of the PCR device according to Example 1 of the present invention and a view depicting a peripheral configuration thereof.

FIG. 2 is a top view of the reaction container of the PCR device according to Example 1 of the present invention and a view depicting a peripheral configuration thereof. A pump 26 injects the reaction solution through the inlet well 17 into the channel 19. A pump 27 discharges the reaction solution within the channel 19 through the outlet well 18. A control section 31 applies an AC voltage necessary for performing a PCR cycle to the electrode pair 22. The AC has a frequency of 10 kHz to 10 MHz, for example, 5 MHz. As compared with a slight amount of reaction solution within the channel 19, large electrodes can be used, and a configuration for directly heating the reaction solution is adopted, and thus a time constant of a response of the reaction solution temperature to voltage application can be provided within 1 second.

As PCR cycles, for example, the following steps are repeatedly performed 20 to 30 cycles in order.
(1) 2 seconds to 10 seconds of denaturation (≈94° C.)
(2) 5 seconds of annealing (54° C. to 60° C.)
(3) 2 seconds to 10 seconds of extension (≈72° C.)

In actuality, a PCR cycle is performed by maintaining an environment surrounding the reaction container at the annealing temperature, and applying in order to reach a denaturation temperature and an extension temperature respectively corresponding AC voltages to the electrode pair 22 to make an AC current flow through the reaction solution and heat the reaction solution by Joule heat to thereby control the temperature of the reaction solution.

Alternatively, a PCR cycle of two steps of performing annealing and extension at the same temperature will suffice.

The present example can carry out any of the following three types of PCR methods. (1) The reaction solution is made to flow continuously or intermittently from the inlet well 17 to the outlet well 18, while the entire reaction solution within the channel 19 is controlled in temperature so as to be a PCR cycle. (2) With the reaction solution injected in the channel 19 and arrested within the channel 19, the entire reaction solution is controlled in temperature so as to be a PCR cycle. (3) The electrode pair 22 is divided into several parts, and an AC voltage corresponding to each step of the PCR cycle is always applied to the respective parts of the electrode pair 22, and the reaction solution is then made to flow continuously or intermittently from the inlet well 17 to the outlet well 18.

In the present example, because an AC current is made to flow through the reaction solution, the AC current does not electrolyze the reaction solution. Moreover, because an electric current is made to flow through a gap between the electrodes along a flow of the reaction solution, the electric current flow is wide in width and short in distance and a load resistance is small, and thus even with low application voltage, Joule heat sufficient for temperature control of a PCR cycle can be generated.

Further, when a channel of the present example is used, as online processing, linkage with a previous stage or subsequent stage of processing is possible. As the previous stage, grinding of cells, extraction and purification of genes, fragmentation of cells, or the like is feasible, while as the subsequent stage, an electrophoresis analysis, a microarray analysis, or a connection to a mass spectrometer is feasible, and further various gene analysis methods can be linked as an integrated device that is connected directly at a microchannel without a tube.

EXAMPLE 2

Figure 3:
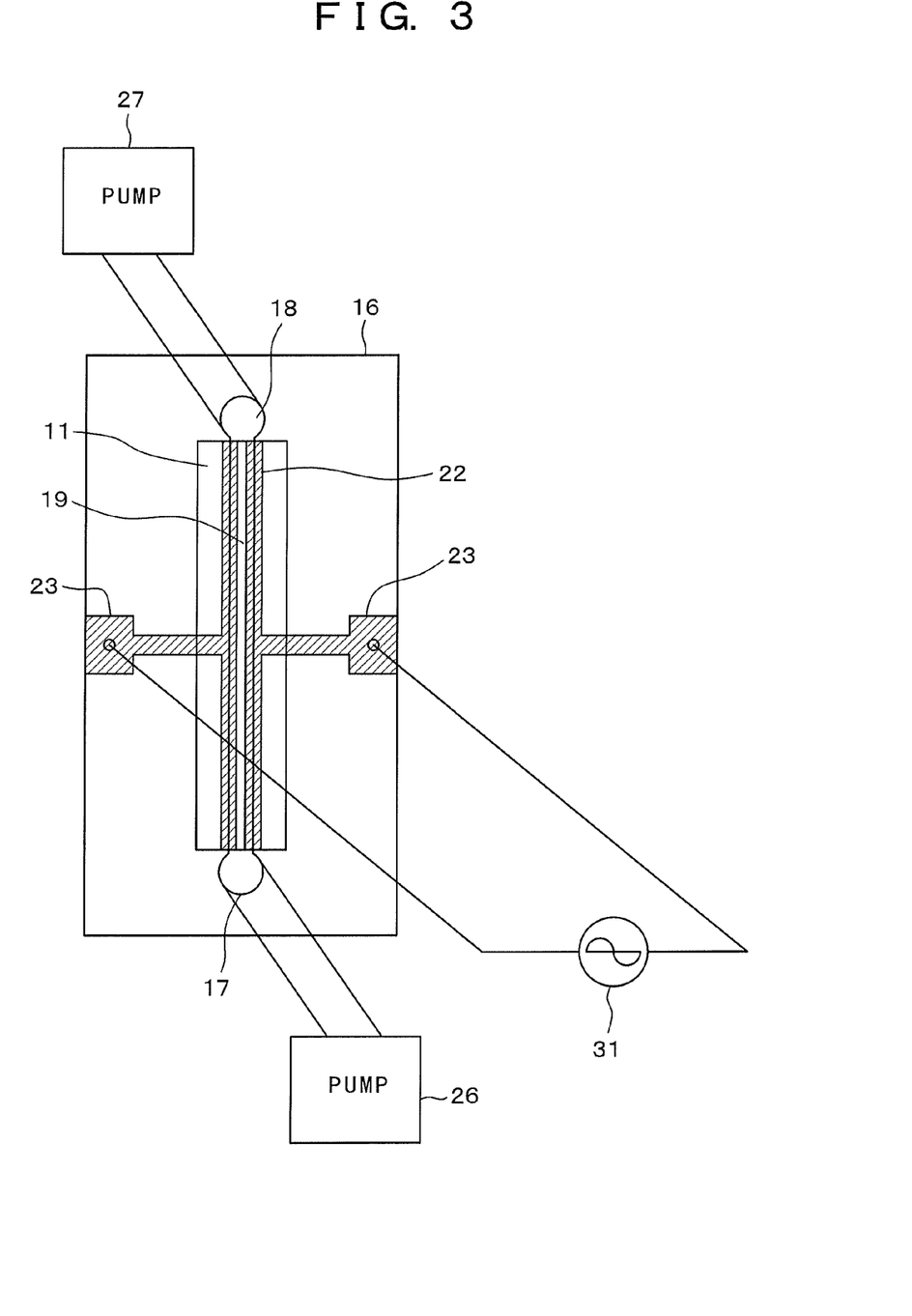
FIG. 3 is a top view of a reaction container of a PCR device according to Example 2 of the present invention and a view depicting a peripheral configuration thereof.

FIG. 3 is a top view of a reaction container of a PCR device according to Example 2 of the present invention and a view depicting a peripheral configuration thereof. For the present example, the reaction container of Example 1 is vertically erected, and the reaction solution is injected from the bottom of the channel 19 and discharged from the top thereof. Because the reaction solution within the channel 19 becomes an upward flow as a result of Joule heating, the reaction solution is sent to flow from the inlet well 17 to the outlet well 18 even without the pumps 26, 27. In addition, by using the pumps 26, 27 in combination, the reaction solution can be sent to flow at a predetermined speed required for a variety of types of PCR methods.

EXAMPLE 3

Figure 4:
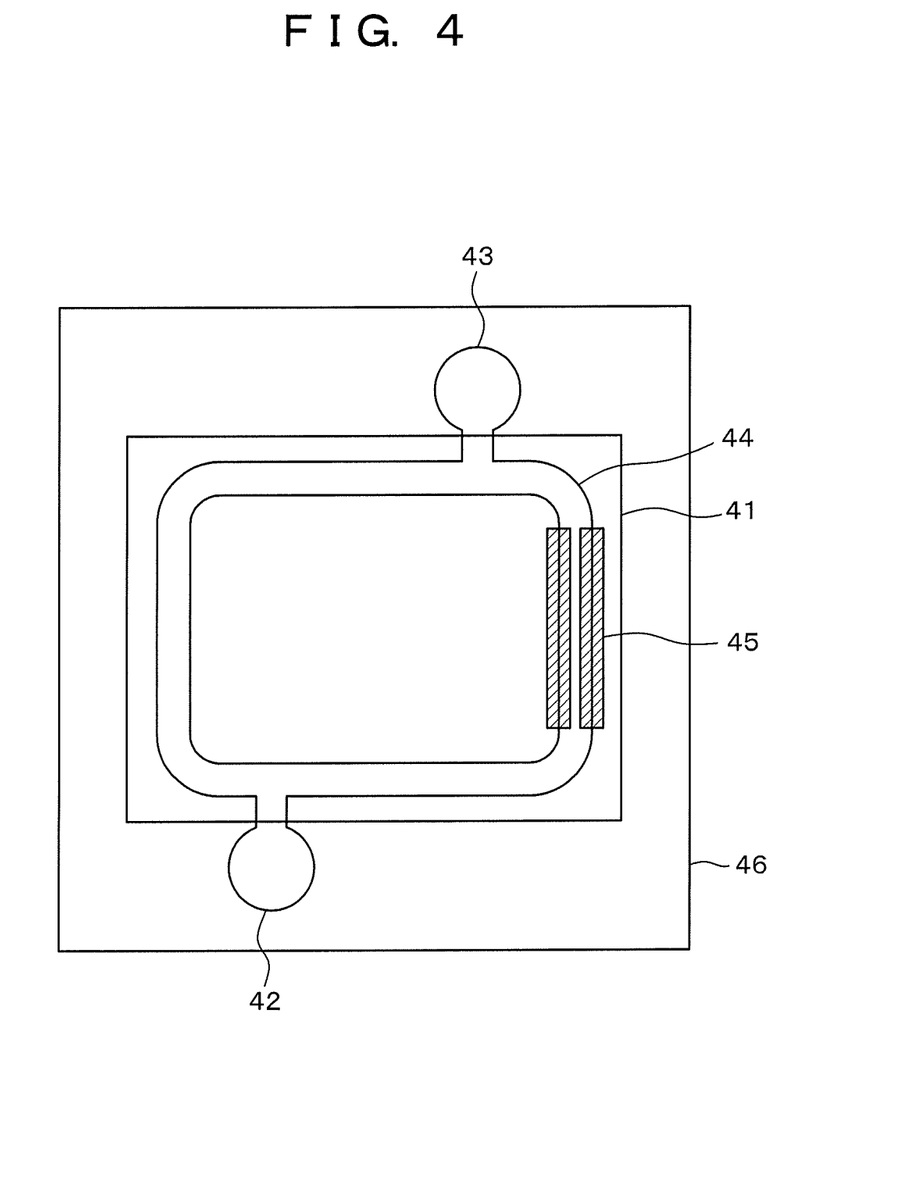
FIG. 4 is a front view of a reaction container of a PCR device according to Example 3 of the present invention.

FIG. 4 is a front view of a reaction container of a PCR device according to Example 3 of the present invention. The PCR device of the present example includes a cover plate 41, an outlet 42, an inlet 43, a channel 44, an electrode pair 45, a channel forming plate 46, and a substrate (not shown in the figure), and the reaction container is vertically erected. Here, the pumps, outgoing portions, and control section are omitted. The channel 44 of the present example has an annular tubular shape. A reaction solution is injected through the inlet 43. The reaction solution is subjected to Joule heating by the electrode pair 45 to reach a denaturation temperature, and made into an upward flow in the periphery of the electrode pair 45 to circulate within the annular channel 44 so as to perform a PCR cycle. A two-step PCR cycle is assumed here. The reaction solution is discharged through the outlet 42 when the PCR is completed. The present example also uses an upward flow of the reaction solution by Joule heating.

EXAMPLE 4

Figure 5:
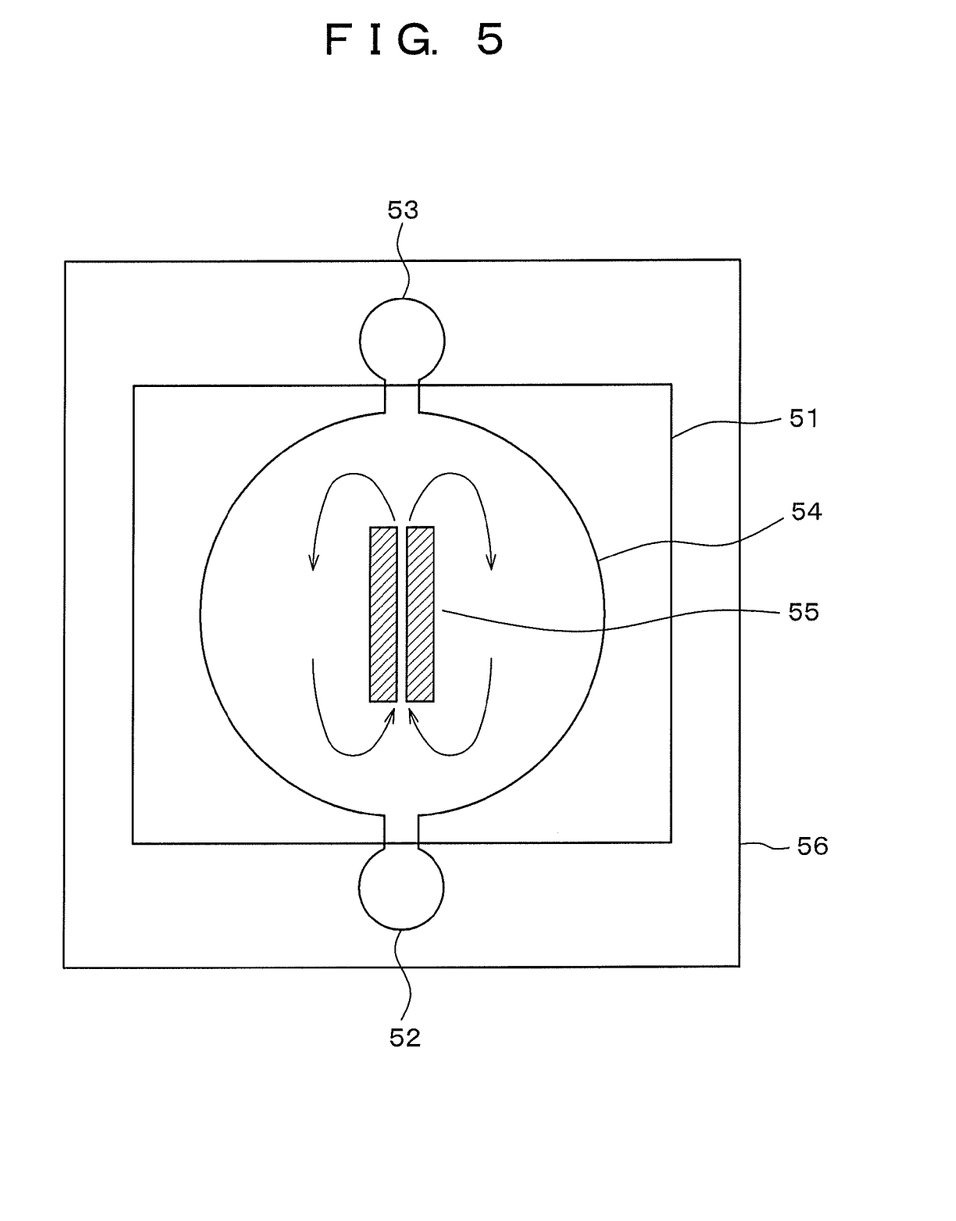
FIG. 5 is a front view of a reaction container of a PCR device according to Example 4 of the present invention.

FIG. 5 is a front view of a reaction container of a PCR device according to Example 4 of the present invention. The PCR device of the present example includes a cover plate 51, an outlet 52, an inlet 53, a chamber 54, an electrode pair 55, a chamber forming plate 56, and a substrate (not shown in the figure), and the reaction container is vertically erected. The cover plate 51 and the substrate are fixed with the chamber forming plate 56 interposed therebetween, and form an upper surface and a lower surface of the chamber 54, respectively. Here, the pumps, outgoing portions, and control section are omitted. The chamber 54 of the present example forms a flat circular space. The electrode pair 55 is provided in the middle of the chamber 54, and a gap between the electrodes is vertically oriented. A reaction solution is injected through the inlet 53. The reaction solution is subjected to Joule heating by the electrode pair 55 to reach a denaturation temperature, and made into an upward flow in the periphery of the electrode pair 55 to circulate in two annular forms within the flat chamber 54 so as to perform a PCR cycle. A two-step PCR cycle is assumed here. The reaction solution is discharged through the outlet 52 when the PCR is completed. The present example also uses an upward flow of the reaction solution by Joule heating.

EXAMPLE 5

Figure 6A:
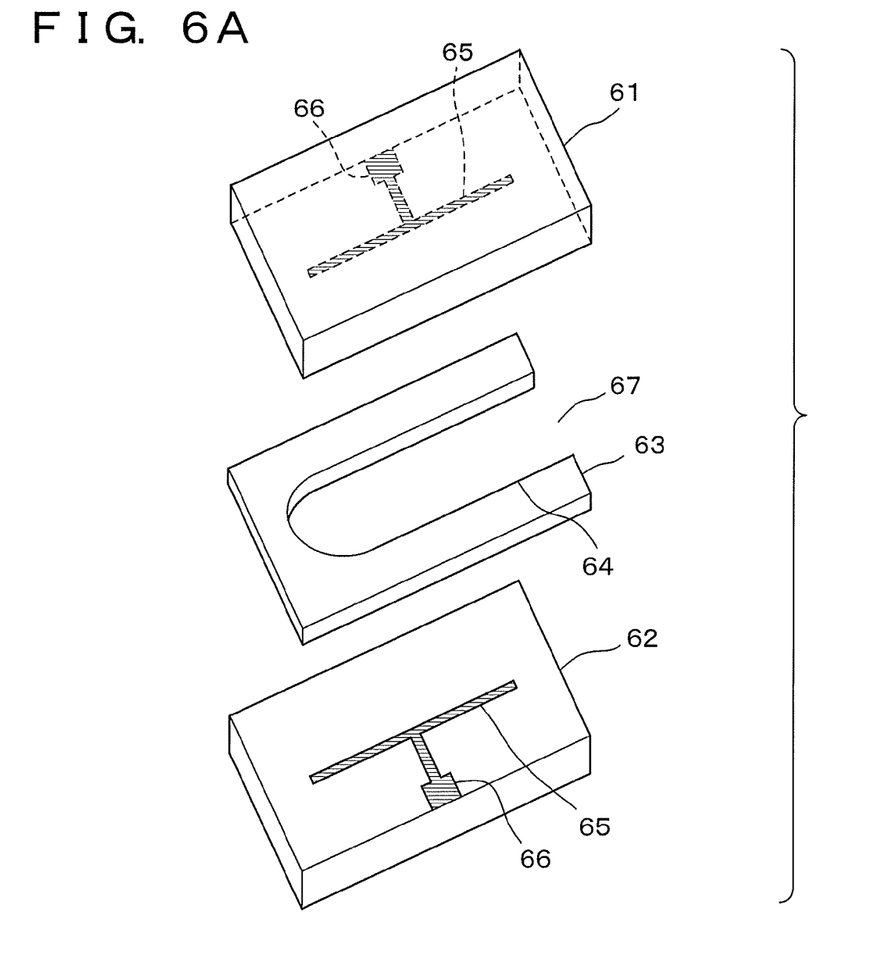
FIG. 6A is an exploded perspective view depicting a configuration of a reaction container of a PCR device according to Example 5 of the present invention.
Figure 6B:
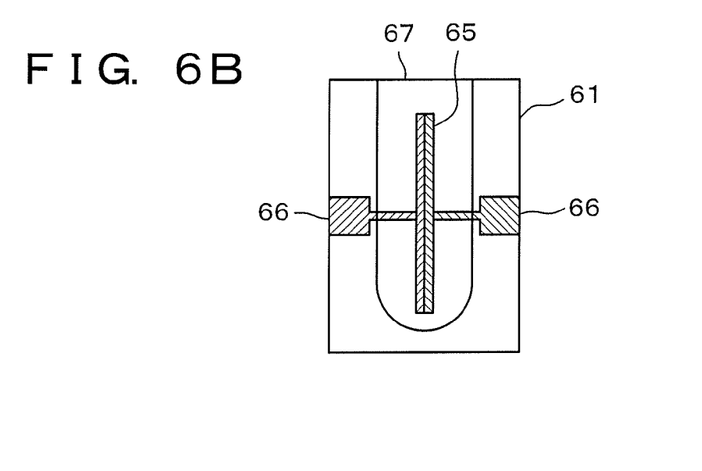
FIG. 6B is a front view of FIG. 6A.

FIG. 6A is an exploded perspective view depicting a configuration of a reaction container of a PCR device according to Example 5 of the present invention, and FIG. 6B is a front view of FIG. 6A. The PCR device of the present example includes an upper substrate 61, a lower substrate 62, a chamber forming plate 63, a chamber 64, an electrode pair 65, an outgoing portion 66, and an inlet-outlet 67, and the reaction container is vertically erected. The upper substrate 61 and the lower substrate 62 are fixed with the chamber forming plate 63 interposed therebetween, and form an upper surface and a lower surface (when viewed from the front) of the chamber 64, respectively. Here, the control section is omitted. One of the electrode pair 65 is disposed on an inner surface of the upper substrate 61, and the other is disposed on an inner surface of the lower substrate 62, and the one and the other of the electrode pair compose, with a reaction solution interposed therebetween, an electrode pair that applies voltage across a section in the middle of the chamber. In the front view of FIG. 6B, the electrode pair 65 is disposed so as not to overlap each other. An electric current accordingly flows from edge to edge of the electrode, which reduces variation in resistance of each electric current path flowing over the longitudinal direction of the electrode to reduce variation in electric current, allowing uniform temperature control. The chamber 64 of the present example forms a flat U-shaped space, and includes the inlet-outlet 67 that is vertically opened. A reaction solution is injected through the inlet-outlet 67 by use of a micropipette or the like. Because the chamber is opened at an upper end thereof in the air, the open end is blocked with mineral oil to prevent evaporation of the reaction solution. The reaction solution is subjected to Joule heating by the electrode pair 65 to reach a denaturation temperature, and made into an upward flow in the periphery of the electrode pair 65 to circulate in two annular forms within the flat chamber 64 so as to perform a PCR cycle. A two-step PCR cycle is assumed here. The reaction solution is discharged through the inlet-outlet 67 by use of a glass capillary or the like when the PCR is completed. The present example also uses an upward flow of the reaction solution by Joule heating. In the case of Examples 1 to 4, electric current is made to flow along the substrate, a large amount of heat escapes through the substrate even after heating, but because electric current is made to flow from one substrate to the other substrate in the middle (the thickness direction) of the chamber in the case of the present example, escaping heat can be reduced to perform temperature control with efficiency. Moreover, in the case of the present example, because the distance of a gap between the electrodes is defined by a spacer being the chamber forming plate, no expensive patterning of an electrode pair is necessary, and an electrode pair can be uniformly manufactured at low cost.

However, the present invention is not limited to the above-described examples.

The material of each component is not limited to the foregoing material, and a component made of a material to be used for a common microchannel can be adopted.

The disclosure of Japanese Patent Application No. 2009-252811, filed on Nov. 4, 2009 including its specification, claims and drawings, is incorporated herein by reference in its entirety.

All the publications, patents and patent applications cited in the present specification are incorporated herein by reference in its entirety.

[Reference Signs List]
41, 51 Cover plate
16, 46 Channel forming plate
17 Inlet well
18 Outlet well
19, 44 Channel
21 Substrate
22, 45, 55, 65 Electrode pair
23, 66 Outgoing portion
24, 25 Through-hole
26, 27 Pump
28, 29 Grommet
31 Control section
42, 52 Outlet
43, 53 Inlet
54, 64 Chamber
56, 63 Chamber forming plate
61 Upper substrate
62 Lower substrate
67 Inlet-outlet

The invention claimed is:

1. A polymerase chain reaction (PCR) method comprising the steps of:
providing, on an inner surface of a container to carry out polymerase chain reaction (PCR), an electrode pair to be disposed to face each other with a gap as part of a flowpath of a reaction solution interposed therebetween;
applying an AC voltage to the electrode pair to make an AC current flow through the reaction solution, thereby generating Joule heat to control the reaction solution in temperature;
flowing the reaction solution intermittently through the gap while the entire reaction solution within the container is controlled in temperature so as to be a complete PCR cycle; and
performing a PCR cycle in the container.

2. A polymerase chain reaction (PCR) method comprising the steps of:
providing, on an inner surface of a container to carry out polymerase chain reaction (PCR), an electrode pair to be disposed to face each other with a gap as part of a flowpath of a reaction solution interposed therebetween;
applying an AC voltage to the electrode pair to make an AC current flow through the reaction solution, thereby generating Joule heat to control the reaction solution in temperature;
arresting the reaction solution in the container such that the entire reaction solution is controlled in temperature so as to be a PCR cycle; and
performing a PCR cycle in the container.

3. A polymerase chain reaction (PCR) method comprising the steps of:
providing, on an inner surface of a container to carry out polymerase chain reaction (PCR), an electrode pair to be disposed to face each other with a gap as part of a flowpath of a reaction solution interposed therebetween;

applying an AC voltage to the electrode pair to make an AC current flow through the reaction solution, thereby generating Joule heat to control the reaction solution in temperature; and performing a PCR cycle in the container, wherein the electrode pair creates an electric field applied in a perpendicular direction compared to a direction of the flowpath.

4. The PCR method according to claim 1, wherein the container is a tubular channel.

5. The PCR method according to claim 1, wherein the channel is vertically oriented.

6. The PCR method according to claim 1, wherein the container is a flat chamber which is vertically erected, and the electrode pair is disposed to face each other with a vertical gap interposed therebetween on inner surface of one of the sidewalls of the chamber.

7. The PCR method according to claim 1, wherein the container is a flat chamber which is vertically erected, and the electrode pair is disposed to face each other, with the chamber interposed as a gap therebetween, on an inner surface of one of the sidewalls of the chamber and an inner surface of the other sidewall.

8. The PCR method according to claim 2, wherein the container is a tubular channel.

9. The PCR method according to claim 2, wherein the channel is vertically oriented.

10. The PCR method according to claim 2, wherein the container is a flat chamber which is vertically erected, and the electrode pair is disposed to face each other with a vertical gap interposed therebetween on inner surface of one of the sidewalls of the chamber.

11. The PCR method according to claim 2, wherein the container is a flat chamber which is vertically erected, and the electrode pair is disposed to face each other, with the chamber interposed as a gap therebetween, on an inner surface of one of the sidewalls of the chamber and an inner surface of the other sidewall.

12. The PCR method according to claim 3, wherein the container is a tubular channel and the channel is vertically oriented.

13. The PCR method according to claim 3, wherein the container is a flat chamber which is vertically erected, and the electrode pair is disposed to face each other with a vertical gap interposed therebetween on inner surface of one of the sidewalls of the chamber.

14. The PCR method according to claim 3, wherein the container is a flat chamber which is vertically erected, and the electrode pair is disposed to face each other, with the chamber interposed as a gap therebetween, on an inner surface of one of the sidewalls of the chamber and an inner surface of the other sidewall.

15. The PCR method according to claim 3, further comprising the step of flowing the reaction solution continuously through the gap while the entire reaction solution within the container is controlled in temperature by the AC current directly heating the reaction solution so as to be a complete PCR cycle.

\* \* \* \* \*